United States Patent [19]
Kobayashi et al.

[11] Patent Number: 6,068,995
[45] Date of Patent: *May 30, 2000

[54] METHOD FOR PRODUCING PROTEIN

[75] Inventors: Kaoru Kobayashi; Kenji Tomomitsu; Shinobu Kuwae; Tomoshi Ohya; Toyoo Ohda; Takao Ohmura, all of Hirakata, Japan

[73] Assignee: Yoshitomi Pharmaceutical Industries, Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/666,435

[22] PCT Filed: Oct. 25, 1994

[86] PCT No.: PCT/JP95/02186

§ 371 Date: Sep. 19, 1996

§ 102(e) Date: Sep. 19, 1996

[87] PCT Pub. No.: WO96/12816

PCT Pub. Date: May 2, 1996

[30] Foreign Application Priority Data

Oct. 25, 1994 [JP] Japan ..................... 6-260728

[51] Int. Cl.[7] .............. C12N 15/18; C12N 1/19
[52] U.S. Cl. ............. 435/71.2; 435/69.6; 435/69.9; 435/69.1
[58] Field of Search ................. 435/69.6, 69.9, 435/69.1, 71.2

[56] References Cited

U.S. PATENT DOCUMENTS 5,139,936  8/1992  Batstein et al. .
5,330,901  7/1994  Prevatt et al. .
5,612,198  3/1997  Brierly et al. .

FOREIGN PATENT DOCUMENTS

WO 92/13951  8/1992  WIPO .
WO 93/22448  11/1993  WIPO .

OTHER PUBLICATIONS

Cress et al Biotechnology 11:905, 1993.
Vedvick et al. J. Ind. Microbiology 7:192, 1991.
Hardjito L. et al., "Recombinant protein production via fed–batch culture of the yeast *Saccharomyces cerevisiae*" Enzyme and Microbial Technology, vol. 15, No. 2, Feb., 1993. pp. 120–126.

*Primary Examiner*—Christina Chan
*Assistant Examiner*—Martha Lubet
*Attorney, Agent, or Firm*—Sughrue, Mion, Zinn, Macpeak & Seas, PLLC

[57] ABSTRACT

A method for producing a desired protein, which comprises growing, by a fed-batch culture, a host cell capable of expressing the desired protein, wherein the specific growth rate of the host cell is changed from the initial rate to a predetermined one by successively changing the rate of addition of a substrate which controls the growth of the host cell. According to the mode of change of the rate of substrate addition to the medium of the present invention, optimal patterns of specific growth rate $\mu$ and specific production rate $\rho$ can be realized to optimize the fed-batch culture system. As a consequence of the realization, it is made possible to perform a high density culture of the host cell by fed-batch culture, an the desired protein can be produced efficiently in a short time.

11 Claims, 3 Drawing Sheets

F I G. 1
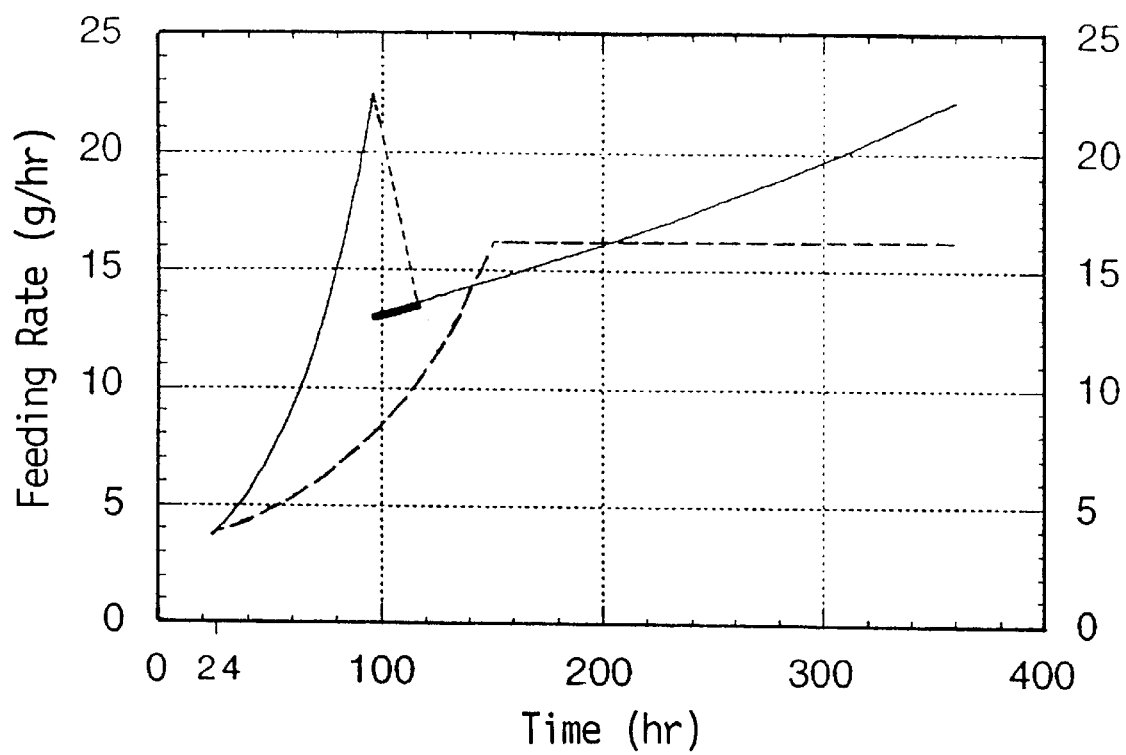

6,068,995

METHOD FOR PRODUCING PROTEIN

This application is as 35 USC 371 national application of PCT JP95/02186.

TECHNICAL FIELD

The present invention relates to a method for producing a protein, comprising controlling the rate of addition of a substrate to a medium during culture process to achieve efficient production of the protein. More particularly, the present invention relates to a method for efficiently producing a protein, comprising controlling the rate of addition of a substrate to a medium to optimize the culture environment of a fed-batch culture system by the use of a specific growth rate $\mu$ as an index.

BACKGROUND ART

Most of the commercially valuable proteins have been currently produced by culture of a host cell capable of expressing the gene of such protein.

The production of a protein by a culture technique or genetic recombination is based on the mechanism allowing production of a desired protein along with the exponential functional proliferation of the host cell. For the productivity of the protein to increase, it is needed to prepare or control the culture environment of the host cell, so that the performance of the host cell (function of cell) can be most effectively utilized. For this end, a variety of methods suitable for culture production have been investigated in terms of the culture process for producing the desired protein in a short time with high production efficiency and high yield.

There is a close relationship between the specific growth rate of the host cell and the amount of the protein produced by said host cell, and the maximum production of the protein requires control of the specific growth rate of the host cell to maintain same at an optimal value. To achieve this, the relationship between the amount of the product produced by the host cell (microorganism) and specific growth rate thereof has been heretofore studied from various aspects, which led to the suggestion of numerous models.

According to these models, it sometimes happens that the specific growth rate of the cell should be varied at least once during culture to increase the amount of production [*Hakko KogakuKaishi*, vol. 70, No. 5, pp. 395–404 (1992)].

However, the studies by the present inventors have firstly revealed that the variation of the specific growth rate aiming at optimization of the culture does not lead to an increase in the amount of production of the objective product to a desired degree (present specification, Example 1).

Hence, a culture method is demanded to increase the productivity of the desired product produced by the host cell, which is capable of efficiently producing the product without affecting the performance of the host cell due to the changes in the specific growth rate of the host cell.

It is therefore an object of the present invention to provide a method for producing a protein, comprising controlling, in a fed-batch culture system, the specific growth rate $\mu$ of the host cell by changing the feeding rate of a substrate into a medium, thereby to produce the desired protein in large amounts in a short time.

Another aspect of the present invention deals with the provision of a method for culturing the host cell capable of producing the desired protein in a highly efficient manner.

DISCLOSURE OF THE INVENTION

The present inventors have investigated the relationship between the rate of substrate feeding into a fed-batch culture and the specific growth rate of the host cell, and further between the rate of feeding and the amount of the produced objective product (protein) to find a method for adjusting or controlling the specific growth rate $\mu$ of the host cell to the optimal value (objective value) without feedback control, and found that successive variation of the rate of feeding the substrate into the medium for the purpose of changing the specific growth rate $\mu$ of the cell during culture leads to an increased productivity of the objective product, without exerting an adverse influence on the cell function or the production of the objective product, which resulted in the completion of the present invention.

That is, the present invention provides a method for producing a desired protein, comprising growth by fed-batch culture of a host cell, preferably a host cell capable of constitutive expression of the desired protein or a host cell capable of substantially constitutive expression of the desired protein when the host cell can proliferate by an inducer, wherein the specific growth rate $\mu$ of the host cell is changed from the initial specific growth rate to a predetermined one by successively changing the rate of addition of the substrate that controls the proliferation of the host cell.

BRIEF EXPLANATION OF THE DRAWINGS

FIG. 1 shows time-course changes of the rate of addition of methanol to a medium (Example 1).

DETAILED DESCRIPTION OF THE INVENTION

Figure 2:
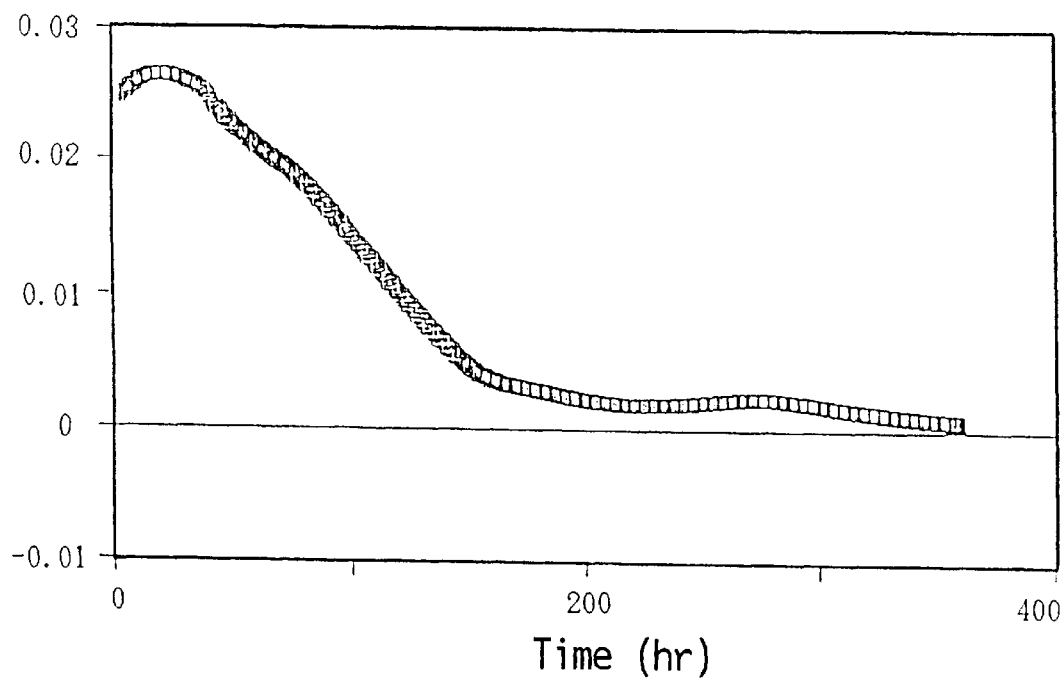
FIG. 2 shows time-course changes of the specific growth rate $\mu$ in the system (the present invention) including successive changes of the addition rate of methanol [Figure (a)], and time-course changes of the specific growth rate $\mu$ in the system (control ①) including an instantaneous change of the addition rate of methanol [Figure (b)].
Figure 2:
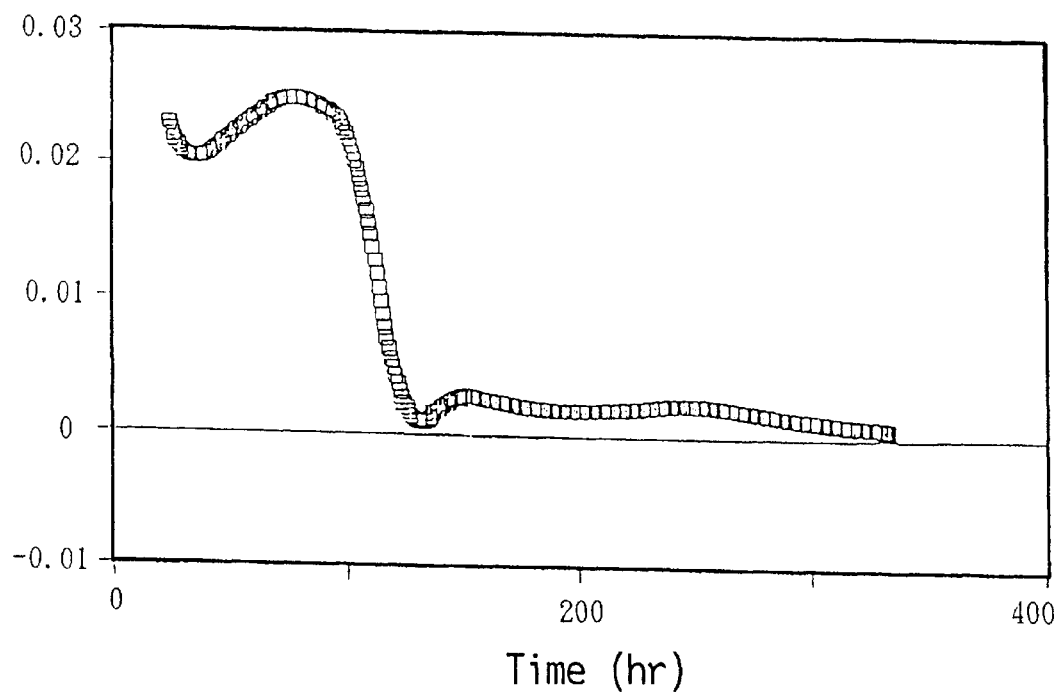

In the present invention, "constitutive expression of the desired protein" means that the desired protein is constantly expressed irrespective of the growth conditions of the host cell.

In the present invention, moreover, "substantially constitutive expression of the desired protein when the host cell can proliferate by an inducer" means that there is some relationship between the growth conditions of the host cell and the expression of the protein, and when the substance needed for the proliferation of the host cell and the inducer are the same, the proliferation of the host cell and the expression of the desired protein occur concurrently.

As used herein, by "an inducer" is meant a substance which initiates the transcription and translation of the gene encoding the desired protein, which is exemplified by methanol, galactose and sucrose.

Examples of the "host cell capable of expressing the desired protein" (hereinafter to be referred to briefly as "host cell") to be used in the present invention include naturally occurring cells and cells mutated to be able to produce a foreign protein (hereinafter also referred to as "transformed cell" as appropriate).

The origin of the host cell is not particularly limited, and the host cell is exemplified by microorganisms such as bacteria (e.g., those belonging to the genus Escherichia and those belonging to the genus Bacillus) and yeast (e.g., the genus Saccharomyces and the genus Pichia). To be specific, the genus Escherichia includes, for example, *Escherichia coli* (hereinafter *E. coli*) K12DH1, M103, JA221, HB101, X600, XL-1 Blue and JM109. The genus Bacillus includes, for example, *Bacillus subtilis* MI114 and 207-21. The yeast includes, for example, *Saccharomyces cerevisiae* AH22, AH22R⁻, NA87-11A and DKD-5D and *Pichia pastoris*. Note that the origin is not limited to those exemplified above. Of those, preferred is yeast.

When a yeast is used as a host cell, it may be a methylotrophic yeast. Examples of suitable methylotrophic yeast include, but not limited to, the yeasts belonging to the genus Hansenula or the genus Pichia, which are capable of growing in methanol [The Biochemistry of Methylotrophs, 269 (1982)]. Preferred are methylotrophic yeasts belonging to the genus Pichia, such as auxotrophic *Pichia pastoris* GTS115 (NRRL Y-15851), *Pichia pastoris* GS190 (NRRL Y-18014), *Pichia Pastoris* PPF1 (NRRL Y-18017), and wild *Pichia pastoris* strain (NRRL Y-11430, NRRL Y-11431).

Preferable host cell includes, for example, transformed cells capable of producing a desired protein heterologous to the host cell (hereinafter referred to as "heterologous protein" as appropriate). Such cells have a foreign DNA encoding the amino acid sequence of the heterologous protein, and express and produce the desired heterologous protein according to said DNA codes. The method for obtaining the cell is not particularly limited. For example, the cell can be obtained using the recombinant DNA technique by transformation with a plasmid or phage carrying the DNA encoding the desired protein.

One specific example of the host cell in the meaning of the present invention is a host cell which produces HSA. The preparation of this cell and the expression and production of HSA using said cell can be performed by a known method or a method according to the known method.

Specific examples of the method include a method using a known human serum albumin gene (Japanese Patent Unexamined Publication Nos. 56684/1983, 90515/1983 and 150517/1983), a method using a novel human serum albumin gene (Japanese Patent Unexamined Publication Nos. 29985/1987 and 98486/1989), a method using a synthetic signal sequence (Japanese Patent Unexamined Publication No. 240191/1989), a method using a serum albumin signal sequence (Japanese Patent Unexamined Publication No. 167095/1990), a method comprising integration of a recombinant plasmid onto a chromosome (Japanese Patent Unexamined Publication No. 72889/1991), a method comprising fusion of hosts (Japanese Patent Unexamined Publication No. 53877/1991), a method comprising mutation in a medium containing methanol, a method using a mutant AOX₂ promoter (Japanese Patent Unexamined Publication No. 299984/1992), a method comprising expression of HSA by *Bacillus subtilis* (Japanese Patent Unexamined Publication No. 25133/1987), a method comprising expression of HSA by yeast (Japanese Patent Unexamined Publication Nos. 41487/1985, 39576/1989 and 74493/1989) and a method comprising expression of HSA by Pichia yeast (Japanese Patent Unexamined Publication No. 104290/1990).

The protein to be the target of the method of the present invention is not particularly limited, and may be any protein such as a constitutive protein of the above-mentioned natural host cell, which protein being produced thereby, and a foreign protein produced by transformed cells.

Specific examples of the constitutive protein of the host cell include RNA polymerase, actin, and enzymes involved in the respiratory system or glycolysis system; and examples of the heterologous protein include interferon, urokinase, prourokinase, t-PA (tissue plasminogen activator), G-CSF (granulocyte•colony stimulating factor), M-CSF (macrophage•colony stimulating factor), HSA (human serum albumin), IGF (insulin-like growth factor) and urinary trypsin inhibitor (UTI), with preference given to HSA, interferon, urokinase, prourokinase, IGF and UTI, and more preference given to HSA.

The combination of the host cell and heterologous protein is subject to no particular limitation and they can be combined as appropriate. A combination of *Escherichia coli* and interferon, that of *Saccharomyces cerevisiae* and prourokinase, that of *Saccharomyces cerevisiae* and HSA, and that of *Pchia pastoris* and HSA are exemplified.

The host cell (transformed cell) may be cultured by fed-batch culture in a medium containing various carbon energy sources and/or nutrients. That is, a host cell is cultured for a certain period in a medium (primary medium) containing various carbon energy sources and/or nutrients suitable for its proliferation, and after a certain point in time, the substrate which controls the proliferation of the host cell is added to said medium, and the culture is completed without removing the objective protein from the system (Japanese Patent Unexamined Publication No. 83595/1991).

The "substrate which controls proliferation of the host cell" in the present invention means a substrate suitable for proliferating the host cell, which can preferably be a carbon energy source.

Examples of the substrate include methanol, glycerine, sorbitol, glucose, fructose, galactose and sucrose, which may be used alone or in combination.

Examples of the preferable substrate to be used when *Pichia pastoris* is used as a host cell include methanol, glycerine, and combinations thereof. Examples of the preferable substrate to be used when *Saccharomyces cerevisiae* is used as a host cell include galactose and sucrose, and examples of the substrate to be used when *Escherichia coli* is used include lactose.

The form of the substrate to be added to the medium may be the substrate itself or a composition including other components such as vitamins and inorganic salts. When added, the substrate may be solid, powder, granule, liquid or in any other form, with preference given to liquid which can quickly and uniformly dissolve in the medium.

The various carbon energy sources and/or nutrients to be used for the primary culture of the host cell are known carbon energy sources and/or nutrients which are suitable for the host cell to be cultured. Examples of the carbon energy source include glucose and glycerine, and examples of the nutrient include nitrogen sources (e.g., yeast extract, bactopeptone, Casamino acid, ammonia, ammonium phosphate and ammonium acetate), phosphate sources (e.g., phosphoric acid and ammonium phosphate), inorganic sources and other trace elements (e.g., iron, zinc, copper, magnesium, manganese, calcium, moribudene and cobalt), and vitamins (e.g., biotin, pantothenic acid and thiamine).

The "successive variation of the rate of the substrate addition" in the present invention means to successively change the rate of the addition of the substrate to the culture tank without lapse. Consequently, the specific growth rate $\mu$ of the host cell moderately changes from the initial rate to a predetermined rate.

The "specific growth rate μ of the host cell" in the present invention means the amount of proliferation of the host cell per unit time (hr) and unit cell amount, which is generally expressed by the following formula:

$$\mu = \frac{1}{XV} \times \frac{\Delta XV}{\Delta t}$$

wherein X is cell density (g/L), V is the amount of medium (L), t is culture time (hr), and ΔXV and Δt are amounts of change in XV and t, respectively.

To change the specific growth rate μ of the host cell from the initial rate to a predetermined rate in the present invention means to change the initial specific growth rate of the host cell to a different, predetermined one during the fed-batch culture. The preferable initial specific growth rate, the predetermined specific growth rate and when to change (i.e., period of time during which the initial specific growth rate is maintained) can be determined from the relationship between the specific growth rate μ and specific production rate ρ [*Hakko KogakuKaishi*, vol. 70, No. 5, pp. 395–404 (1992)].

The specific production rate ρ here means the amount increased in the production of protein per unit time (hr) and unit cell amount, which is generally expressed by the following formula:

$$\rho = \frac{1}{XV} \times \frac{\Delta PV}{\Delta t}$$

wherein P is the amount of the protein produced (g/L), V is the amount of medium (L), t is culture time (hr), and ΔPV and Δt are amounts of change in PV and t, respectively.

The specific growth rate may be changed plural times.

The culture temperature to be used in the present invention is preferably suitable for the proliferation of the host cell and the production of the desired protein, which vary depending on the host cell to be cultured. When the host cell is *Escherichia coli*, the temperature is 20–46° C., preferably 36–38° C.; when it is yeast, the temperature is about 20–35° C., preferably about 23–30° C.; and when it is *Bacillus subtilis*, the temperature is 28–40° C., preferably 36–38° C.

The pH of the medium can be adjusted to a value suitable for the proliferation of the host cell and production of the desired protein, which vary depending on the host cell to be cultured. The dissolved oxygen content of the culture tank is appropriately selected from the range of about 10–70% of the saturation.

The present invention is explained in more detail by referring to Examples and Reference Examples, which are not to be construed as limitative.

EXAMPLE 1

HSA was produced in a culture system comprising change of the specific growth rate μ of the Pichia yeast UHG42-3 strain capable of expression•production of HSA from the initial specific growth rate μ'=0.025 to the predetermined specific growth rate μ"=0.002, the preparation of the strain being described in Japanese Patent Unexamined Publication No. 29984/1992. Specifically, culture comprised the following steps.

(1) Culture method
① Preculture

The strain was precultured in a YPD broth (2% bactopeptone, 1% yeast extract, 2% glucose). To be specific, 1 ml of a cell suspension ($OD_{540}$≈10) of Pichia yeast UHG42-3 freeze-stored in 20% glycerol was inoculated into a 300 ml Erlenmeyer flask with baffles, which contained 50 ml of the YPD broth, and subjected to shake culture at 30° C. for 24 hours.

② Main culture

The broth was subjected to batch culture for a predetermined time in a medium (primary medium) having a composition shown in Table 1, and then cultured with successive addition of methanol at a feeding rate shown in FIG. 1.

TABLE 1

| Composition of primary medium | |
|---|---|
| Ingredient | Concentration (/l) |
| glycerol | 40.0 g |
| $H_3PO_4$ (85%) | 14.0 ml |
| $CaSO_4$ $2H_2O$ | 0.6 g |
| $K_2SO_4$ | 9.5 g |
| $MgSO_4$ $7H_2O$ | 7.8 g |
| KOH | 2.6 g |
| 0.2 g/l biotin solution | 1.6 ml |
| YTM solution* | 4.4 ml |
| Composition of YTM solution* | |
| Ingredient | Concentration (g/l) |
| $FeSO_4$ $2H_2O$ | 65.0 |
| $CuSO_4$ $5H_2O$ | 6.0 |
| $MnSO_4$ $4-5H_2O$ | 4.11 |
| $ZnSO_4$ $7H_2O$ | 20.0 |
| $H_2SO_4$ | 5.0 (ml) |

To be specific, the preculture liquid (34 ml) was inoculated into a 10 L jar fermenter (Biomaster D type, 10 L) containing 1.7 L of batch medium (primary medium) and subjected to aeration agitation culture. The culture temperature was 30° C. The agitation speed was kept constant at 900 rpm during the batch culture. The pH was constantly adjusted to 5.85.

For defoaming, a defoaming agent was added as necessary.

When glycerol in the primary medium was completely consumed (24 hours of culture) during the batch culture, the addition of methanol was initiated.

The addition rate of methanol was controlled according to the following formulas wherein t means the lapse of time (hr) after the initiation of the methanol addition:

when 0≤t<72, F(t)=3.712×exp(0.025×t) (g/hr)

when 72≤t<92, F(t)=22.456×exp[−0.025×(t−72)]

when 92≤t, F(t)=13.62×exp[0.002×(t−92)]

The time-course changes of the addition rate of methanol are shown in FIG. 1, wherein from about hour 24 to hour 96 of culture is shown with a full line; from about hour 96 to hour 116 of culture is shown with a fine broken line; and from about hour 116 to hour 360 of culture is shown with a full line.

During the culture of from about hour 24 (initiation time of methanol addition) to about hour 96, methanol was added to make the initial specific growth rate μ' of Pichia yeast 0.025, and the addition rate of methanol was once moderately or gradually decreased as shown by the fine broken line in the figure, and methanol was added to successively make the predetermined specific growth rate μ" of Pichia yeast 0.002.

As a control experiment, ① culture in a system wherein μ was changed from 0.025 to 0.002 by instantaneously changing the addition rate and ② culture in a system without changing μ were performed.

For changing μ in ①, the addition rate of methanol in the system comprising instantaneous change of addition rate of methanol was controlled according to the following formulas, wherein t means the lapse of time (hr) after initiation of methanol addition, which is expressed by a full line and a thick full line in FIG. 1:

when 0≦t <72, F(t)=3.712×exp(0.025×t) (g/hr)

when 72≦t, F(t)=13.086×exp[0.002×(t-72)]

During the culture of from about hour 24 (initiation time of methanol addition) to about hour 96, methanol was added to make the initial specific growth rate $\mu'$ of Pichia yeast 0.025, and for changing the specific growth rate $\mu''$ of Pichia yeast to 0.002, the addition rate of methanol was instantaneously changed to control μ to 0.002.

The addition rate of methanol in the system ② without change in μ was controlled according to the following formulas wherein t means the lapse of time (hr) after the initiation of methanol addition. The control according to the following formulas is the appropriate culture method in the system without changing μ. That is, feeding is initiated to make μ0.015, and when the dissolved oxygen concentration (concentration of oxygen dissolved in the culture liquid) became lower than a certain level, constant rate feeding is initiated. The time-course changes of the addition rate of methanol in this system are expressed by a broken line in FIG. 1:

when 0≦t<127, F(t)=2.176×exp(0.015×t)+1.632 (g/hr)

when 127≦t, F(t)=16.253

FIG. 2 shows a comparison of the changes in μ in the system comprising successive change in the addition rate of methanol [the present invention, FIG. 2(a)] and the changes in μ in the system comprising instantaneous change of the addition rate [control ①, FIG. 2(b)].

Figure 3:
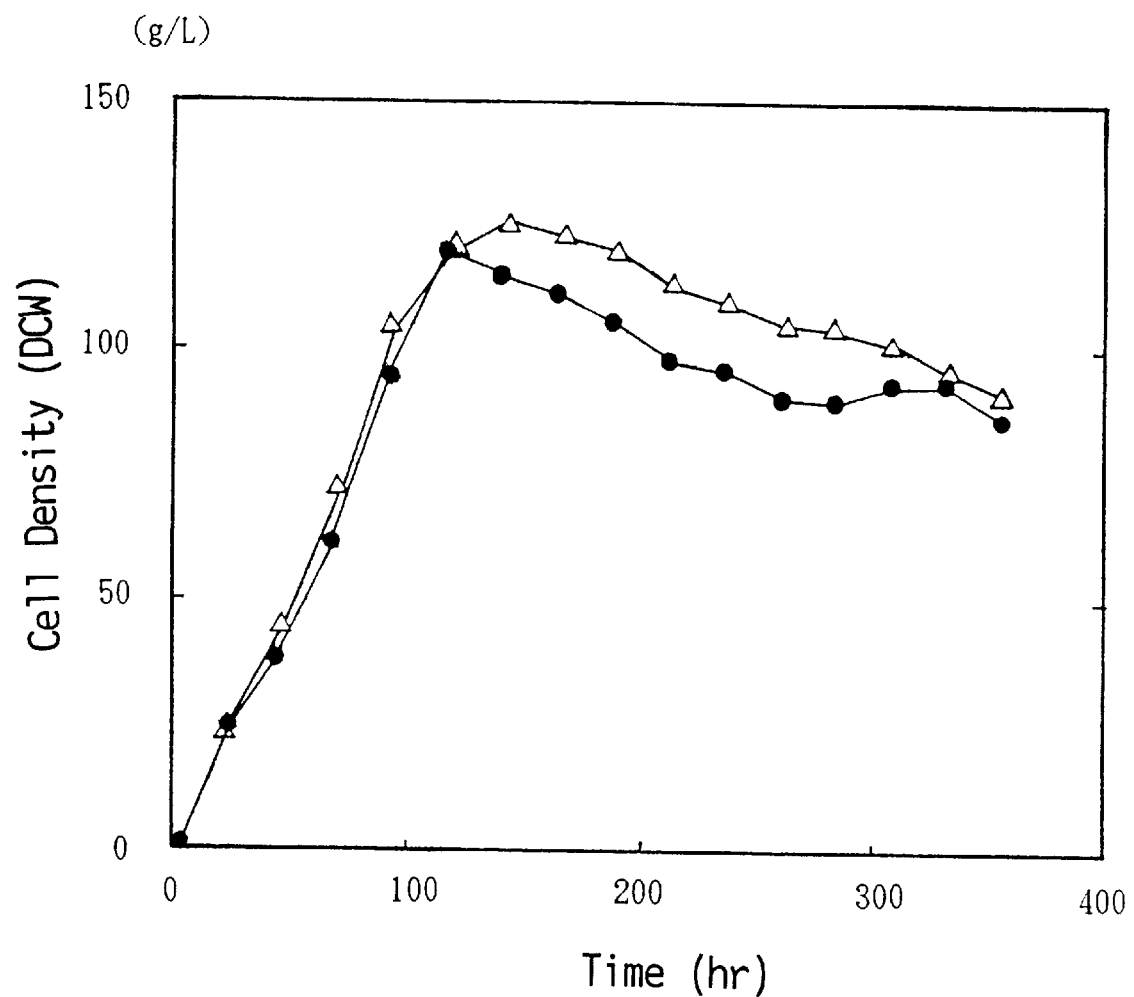
FIG. 3 shows a comparison of the density of the growing cells in the system wherein the rate of methanol addition is successively changed (the present invention, -Δ-) and in the system wherein said rate is instantaneously changed (control ①, -●-).

The results of each culture are shown in FIG. 3 as the time-course changes of cell density (the present invention and control ①) and Table 2 shows the ratio of HSA production at the completion of the culture (the present invention, control ① and control ②).

TABLE 2

| Culture system | | HSA production |
|---|---|---|
| change of μ | change of addition rate | ratio |
| None (control ②) | — | 100% |
| done | instantaneous change (control ①) | 107% |
| done | successive change (present invention) | 156% |

Comparison of the amount of HSA produced after 360 hours of culture reveals that, while the culture showed better results when μ was changed (the present invention, control ①) than when not (control ②), the amount of HSA produced was greater (156%) in the system comprising successive change of the feeding rate (the present invention) than in the case where the feeding rate was instantaneously changed (control ①, 107%), whereby it was clarified that the successive change of the feeding rate of the substrate (methanol) in an attempt to change μ led to an increased amount of the desired protein (HSA) produced.

EXAMPLE 2

In the same manner as in Example 1 except that the feed medium shown in Table 3 was used instead of methanol in the main culture, the strain was cultured.

The results were similar to those obtained in Example 1.

TABLE 3

| Feed medium compositon | |
|---|---|
| Ingredient | Amount (ml) |
| YTM solution | 2 |
| methanol | 1000 |

REFERENCE EXAMPLE 1

Measurement of Cell Density

A culture liquid was sampled after an optional culture time, diluted with distilled water to make the $OD_{540}$ value upon determination not more than 0.3, and subjected to absorbance determination at 540 nm using a spectrophotometer (UV 2200 type, Shimazu Corporation). The obtained value was multiplied by the dilution ratio and used as the absorbance of the culture liquid. Based on a formula $OD_{540}$ value/5.6 ($OD_{540}$=5.6 corresponds to 1 g of dry cells), dry cell density was calculated from the obtained absorbance.

REFERENCE EXAMPLE 2

Measurement of HSA Concentration

A culture liquid was sampled after an optional culture time and centrifuged at 15,000 rpm for 5 minutes. The obtained supernatant was filtered through ultrafree C3HV to give a clear solution, which was subjected to gel filtration by HPLC under the following conditions.

Column: TSKgel $G3000SW_{x1}$

Mobile phase: 0.3 M NaCl, 50 mM sodium phosphate, 0.1% $NaN_3$, pH 6.5

Flow rate: 1.0 ml/min

Injection: 50 μl

Detection: $A_{280}$, $A_{350}$ (two wavelengths)

REFERENCE EXAMPLE 3

Measurement of Methanol Concentration

A culture liquid was sampled after an optional culture time and centrifuged at 15,000 rpm for 5 minutes. The obtained supernatant was filtered through ultrafree C3HV to give a clear solution, which was subjected to quantitative analysis by HPLC under the following conditions.

Column: Sugar-pak Ca (manufactured by Waters)

Mobile phase: 0.02% $NaN_3$

Column temperature: 80° C.

Injection: 28 μl

Detection: differential refractometer

Industrial Applicability

According to the mode of change of the rate of substrate addition to the medium of the present invention, optimal patterns of specific growth rate μ and specific production rate ρ can be realized to optimize the fed-batch culture system. As a consequence of the realization, it has been made possible to perform a high density culture of the host cell by fed-batch culture, and the desired protein can be produced efficiently in a short time.

Therefore, the method of the present invention is extremely useful as an industrial production method of proteins such as HSA, IGF, prourokinase and UTI, having high commercial values.

What is claimed is:

1. A method for producing a desired protein which comprises growing by a fed-batch culture, a host cell which expresses the desired protein, wherein the specific growth rate of the host cell is changed from an initial specific rate to a second predetermined rate by decreasing the feeding rate of a substrate which controls the growth of the host cell, in a manner such that the feeding rate is gradually decreased as a continuous function when expressed as a function of time from a first increasing feeding rate to a second increasing feeding rate.

2. The method of claim 1, wherein the host cell constitutively expresses the desired protein or the host cell substantially constitutively expresses the desired protein when the host cell proliferates under control of an inducer.

3. The method of claim 1, wherein the host cell is derived from a yeast.

4. The method of claim 1, wherein the host cell is derived from a methylotrophic yeast.

5. The method of claim 1, wherein the host cell is derived from Pichia yeast.

6. The method of any one of claim 1 to claim 5, wherein the desired protein is heterologous to the host cell.

7. The method of claim 6, wherein the heterologous protein is human serum albumin.

8. The method of claim 1, wherein the substrate which controls the growth of the host cell is a carbon energy source suitable for the host cell proliferation.

9. The method of claim 8, wherein the carbon energy source is a member selected from the group consisting of methanol, glycerine, sorbitol, glucose, fructose, galactose and sucrose.

10. The method of claim 1, wherein the host cell is derived from Pichia yeast, ant the substrate which controls the growth of the host cell is a member selected from the group consisting of methanol, glycerin and combination thereof.

11. The method of claim 1, wherein the host cell is derived from the genus Saccharomyces, and the substrate which controls the growth of the host cell is a member selected from the group consisting of glucose, sucrose and combinations thereof.

* * * * *